(12) United States Patent
Lyngso

(10) Patent No.: US 7,582,780 B2
(45) Date of Patent: Sep. 1, 2009

(54) METHOD FOR THE SEPARATION OF INTERMEDIATES WHICH MAY BE USED FOR THE PREPARATION OF ESCITALOPRAM

(75) Inventor: Lars Ole Lyngso, Vekso Sj. (DK)

(73) Assignee: H. Lundbeck A/S, Copenhagen-Valby (DK)

( * ) Notice: Subject to any disclaimer, the term of this patent is extended or adjusted under 35 U.S.C. 154(b) by 0 days.

(21) Appl. No.: 10/597,836

(22) PCT Filed: Feb. 2, 2005

(86) PCT No.: PCT/DK2005/000075

§ 371 (c)(1),
(2), (4) Date: Nov. 8, 2006

(87) PCT Pub. No.: WO2005/077891

PCT Pub. Date: Aug. 25, 2005

(65) Prior Publication Data

US 2007/0190624 A1    Aug. 16, 2007

Related U.S. Application Data

(60) Provisional application No. 60/544,970, filed on Feb. 12, 2004.

(30) Foreign Application Priority Data

Feb. 12, 2004  (DK) ................ 2004 00217

(51) Int. Cl.
C07D 307/87 (2006.01)
(52) U.S. Cl. ............... 549/467; 549/504; 548/146; 548/239; 558/422
(58) Field of Classification Search ............. 435/126; 549/504, 469, 467; 548/146, 239; 558/422
See application file for complete search history.

(56) References Cited

U.S. PATENT DOCUMENTS 4,136,193 A    1/1979   Bogeso et al.
4,943,590 A    7/1990   Boegesoe et al.
RE34,712 E     8/1994   Boegesoe et al.
6,407,267 B1   6/2002   Rock et al.

FOREIGN PATENT DOCUMENTS

| EP | 347 066 | 12/1989 |
|---|---|---|
| ES | 2068891 T | 5/1995 |
| ES | 2169709 | 7/2002 |
| WO | 00012044 | 3/2000 |
| WO | WO-00/11926 A2 | 3/2000 |
| WO | WO-00/13648 A2 | 3/2000 |
| WO | WO-00/23431 A1 | 4/2000 |
| WO | WO-01/02383 A2 | 1/2001 |
| WO | WO-01/43525 A2 | 6/2001 |
| WO | WO-01/51478 A1 | 7/2001 |
| WO | WO-01/68629 | 9/2001 |
| WO | WO-01/68630 A1 | 9/2001 |
| WO | WO-01/68631 A1 | 9/2001 |
| WO | WO-01/68632 A1 | 9/2001 |
| WO | WO-03/000672 | 1/2003 |
| WO | WO-03087081 | 10/2003 |
| WO | WO-2004/014821 | 2/2004 |

OTHER PUBLICATIONS

Speciality Chemicals Magazine, Apr. 2003, p. 36-38.
Solares L.F., et al., "Enzymatic Resolution of a Quaternary Stereogenic Centre as the Key Step in the Synthesis of (S)-(+)-Citopram", Tetrahedron: Asymmetry, Elsevier Science Publishers, Amsterdam, NL vol. 15, No. 2, Jan. 26, 2004, p. 341-345.

*Primary Examiner*—Bernard Dentz
*Assistant Examiner*—David E Gallis
(74) *Attorney, Agent, or Firm*—Darby & Darby, P.C.

(57) ABSTRACT

The invention relates to a method of separating and isolating an acylated derivative of 4-[(S)-4-dimethylamino-1-(4-fluorophenyl)-1-hydroxybutyl]-3-hydroxymethylbenzonitrile by reaction of a mixture of the 4-[(S)-4-dimethylamino-1-(4-fluorophenyl)-1-hydroxy-butyl]-3-hydroxymethylbenzonitrile and an acylated derivative thereof with a compound which form a derivative of the 4-[(S)-4-dimethylamino-1-(4-fluorophenyl)-1-hydroxy-butyl]-3-hydroxymethylbenzonitrile containing a carboxylic acid group. The acylated derivative containing a carboxylic acid group precipitates once it is formed and may easily be separated from the reaction mixture.

42 Claims, No Drawings

METHOD FOR THE SEPARATION OF INTERMEDIATES WHICH MAY BE USED FOR THE PREPARATION OF ESCITALOPRAM

CROSS-REFERENCE TO PRIOR APPLICATION

This is a U.S. National Phase Application under 35 U.S.C. 371 of International Patent Application No. PCT/DK2005/000075, filed Feb. 2, 2005, which claims the benefit of Danish Patent Application No. PA 2004 00217, filed Feb. 12, 2004, and U.S. Provisional Patent Application No. 60/544,970, filed Feb. 12, 2004. The International Application published in English on Aug. 25, 2005 as WO 2005/077891 A1 under PCT Article 21(2).

The present invention relates to a novel method for the preparation of optically active intermediates useful for the preparation of escitalopram.

BACKGROUND OF THE INVENTION

Citalopram is a well-known antidepressant drug that has now been on the market for some years.

It is a selective, centrally acting serotonin (5-hydroxytryptamine; 5-HT) reuptake inhibitor, accordingly having antidepressant activities.

Citalopram was first disclosed in DE 2,657,013, corresponding to U.S. Pat. No. 4,136,193. This patent publication i.a. outlines a process for preparation of citalopram from the corresponding 5-bromo-derivative by reaction with cuprous cyanide in a suitable solvent and by alkylation of 5-bromophtalane.

U.S. Pat. No. 4,943,590 corresponding to EP-B1-347 066 describes two processes for the preparation of escitalopram (S-enantiomer of citalopram). Both processes use the racemic diol having the formula

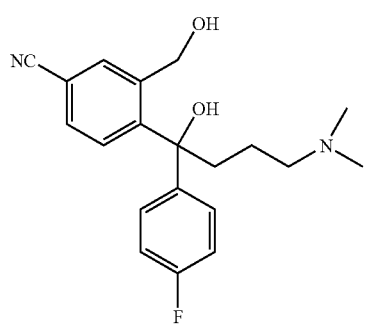

(I)

as starting material. According to the first process, the diol of formula (I) is reacted with an enantiomerically pure acid derivative, such as (+) or (−)-α-methoxy-α-trifluoromethylphenylacetyl chloride to form a mixture of diastereomeric esters, which are separated by HPLC or fractional crystallization, whereupon the ester with the correct stereochemistry is enantioselectively converted into escitalopram. According to the second process, the diol of formula (II) is separated into the enantiomers by stereoselective crystallization with an enantiomerically pure acid such as (+)-di-p-toluoyltartaric acid, whereupon the S-enantiomer of the diol of the formula (I) is enantioselectively converted to escitalopram.

Escitalopram has now been developed as an antidepressant. Hence, there is a desire for an improved method for preparation of escitalopram.

It has been found that the S-enantiomer of the diol of formula (I) above as well as acylated derivatives thereof may be prepared by selective enzymatic acylation of the primary hydroxyl group in the racemic diol to obtain S-diol of formula (I) or an acylated derivative thereof with high optical purity and further that the enantiomers obtained may be effectively separated by reaction of the diol of formula (I) with a compound which form a derivative of the diol of formula (I) containing a carboxylic acid group. The derivative formed precipitates once it is formed and may easily be separated from the reaction mixture.

THE INVENTION

Accordingly, one object of the present invention relates to a method for the isolation and purification of a compound having the formula

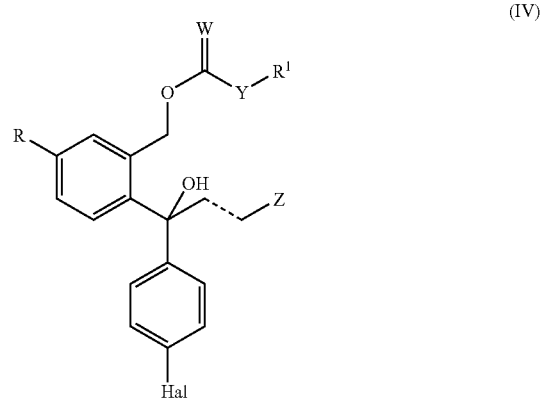

(IV)

wherein R is cyano or a group which may be converted to a cyano group, the dotted line represents a double or single bond, Hal is halogen, Z is a dimethylaminomethyl group or Z is a group which may be converted to a dimethylaminomethyl group, W is O or S, and Y is a bond, O, S or NH and $R^1$ is $C_{1-10}$-alkyl, $C_{2-10}$-alkenyl or $C_{2-10}$-alkynyl all of which may optionally be substituted with one or more substituents selected from $C_{1-10}$-alkoxy, $C_{1-10}$-alkylthio, hydroxy, halogen, amino, nitro, cyano, $C_{1-10}$-alkylamino, di-($C_{1-10}$-alkyl) amino, aryl, aryloxy, arylthio and heteroaryl, or $R^1$ is aryl, wherein any of the aryl and heteroaryl groups may optionally be substituted one or more times with substituents selected from $C_{1-10}$-alkyl, $C_{2-10}$-alkenyl, $C_{2-10}$-alkynyl, $C_{1-10}$-alkoxy, $C_{1-10}$-alkylthio, hydroxy, halogen, amino, nitro, cyano, $C_{1-10}$-alkylamino and di-($C_{1-10}$-alkyl)amino, or a salt thereof and/or a diol of formula

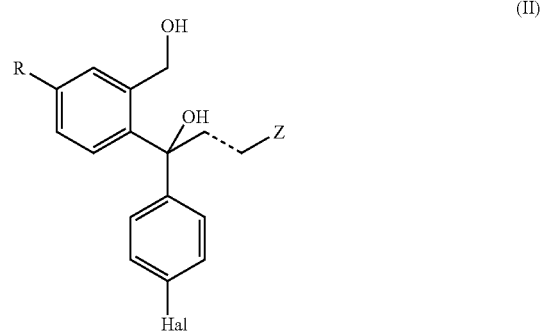

(II)

wherein R, Z, Hal and the dotted line are as defined above, or a salt thereof, from a mixture containing the compound of formula (IV) and the diol of formula (II), which comprises:

a) reacting said mixture containing the compound of formula (IV) and the diol of formula (II) with a cyclic anhydride or imide of formula

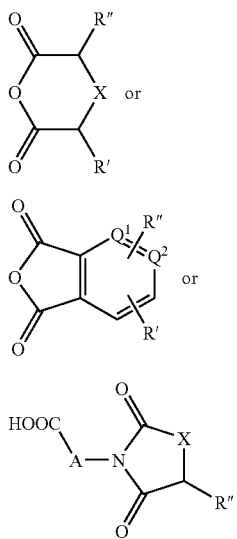

wherein X is —(CHR''')$_n$—, wherein n is 0-2;

and R', R'' and R''' are independently selected from hydrogen, $C_{1-6}$-alkyl, $C_{1-6}$-alkoxy, aryloxy, $C_{1-6}$-acyloxy, aryl-CO—O, wherein each aryl may be substituted with $C_{1-6}$-alkyl, or R' and R'' in an anhydride of formula (Ia) together are —O—CR$^4$R$^5$—O—, wherein R$^4$ and R$^5$ are independently hydrogen or $C_{1-6}$-alkyl, or R' and R'' in an anhydride of formula (Ib) are adjacent and together with the two carbon atoms to which they are attached form a benzene ring;

one of Q$^1$ and Q$^2$ is nitrogen and the other carbon, or both are carbon;

A is $C_{1-6}$-alkylene, phenylene, or naphthylene wherein the $C_{1-6}$-alkylene, phenylene, or naphthylene groups may optionally be substituted one or more times with $C_{1-6}$-alkyl;

to form a mixture of the compound of formula (IV) and an ester having the formula

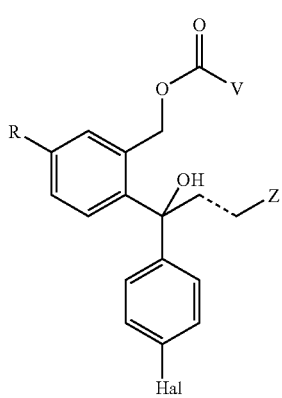

wherein R, Z and Hal is as defined above and V is —CHR'—X—CR''—COOH, —X—CHR''—CO—NH-A-COOH, —CHR''—X—CO—NH-A-COOH or

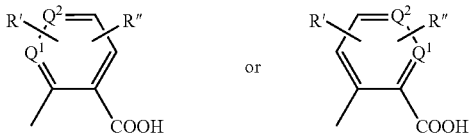

wherein R', R'', X and A are as defined above;

b) separating the compound of formula (IV) from the ester of formula (V) by a method selected from the group consisting of:

i) allowing the acid of formula (V) or a salt thereof to precipitate from the reaction mixture, and separating the precipitate of the compound of formula (V) or a salt thereof from the reaction mixture, optionally followed by isolation of the compound of formula (IV) or a salt thereof from the reaction mixture;

ii) partitioning between an organic solvent and an aqueous solvent whereby the compound of formula (IV) will be dissolved in the organic phase whereas the compound of formula (V) will be dissolved in the aqueous phase, separating the phases, and optionally isolating the compound of formula (IV) or a salt thereof and/or isolating the compound of formula (V) or a salt thereof; and iii) adsorbing the compound of formula (V) on a basic resin, separating the solvent containing the compound of formula (IV) from the resin, desorbing the compound of formula (V) from the basic resin, and optionally isolating the compound of formula (IV) or a salt thereof and/or isolating the compound of formula (V) or a salt thereof.

A second object of the invention relates to a method for the manufacture of escitalopram comprising the method described above.

According to one particular embodiment of the invention, one enantiomer of formula (II) is separated from a compound of formula (IV) in the form of the other enantiomer.

According to one embodiment of the invention the S-enantiomer of the compound of formula (V) or a mixture of enantiomers of the compound of formula (V) comprising more than 50% of the S-enantiomer of the compound of formula (V) is separated from the R-enantiomer of the acyl derivative of formula (IV) or from a mixture of enantiomers of the acyl derivative of formula (IV) comprising more than 50% of the R-enantiomer of the acyl derivative of formula (IV).

According to a particular embodiment of the invention the S-enantiomer of the compound of formula (V) is separated from the R-enantiomer of the acyl derivative of formula (IV) or from a mixture of enantiomers of the acyl derivative of formula (IV) comprising more than 50% of the R-enantiomer of the acyl derivative of formula (IV).

According to a more particular embodiment of the invention the S-enantiomer of the compound of formula (V) is separated from the R-enantiomer of the acyl derivative of formula (IV).

According to another embodiment of the invention, the S-enantiomer of the acyl derivative of formula (IV) or a mixture of enantiomers of the acyl derivative of formula (IV) comprising more than 50% of the S-enantiomer of the acyl derivative of formula (IV) is separated from the R-enantiomer of the compound of formula (V) or from a mixture of enantiomers of the compound of formula (V) comprising more than 50% of the R-enantiomer of the compound of formula (V).

According to a particular embodiment of the invention, the S-enantiomer of the acyl derivative of formula (IV) is separated from the R-enantiomer of the compound of formula (V) or from a mixture of enantiomers of the compound of formula (V) comprising more than 50% of the R-enantiomer of the compound of formula (V).

According to a more particular embodiment, the S-enantiomer of the acyl derivative of formula (IV) is separated from the R-enantiomer of the compound of formula (V).

According to one specific embodiment of the invention, the reagent used is a compound of formula (Ia), suitably succinic anhydrid or glutaric anhydrid.

According to another specific embodiment, the reagent used is a compound of formula (Ib), suitably phtalic acid anhydride.

According to a third embodiment of the invention, the reagent is an imide of Formula (Ic), suitably N-phenyl-succinimide substituted in the phenyl ring with a carboxy group.

According to a further embodiment of the invention, the R group in the compound of formula (V) obtained in the form of the S-enantiomer is optionally converted to cyano, the Z group in the compound of formula (V) obtained is optionally converted to a dimethylaminomethyl group, Hal is optionally converted to fluoro and/or a dotted line representing a double bond is optionally converted to a single bond, in either order; followed by conversion of the compound of formula (V) to escitalopram or a derivative thereof having the formula

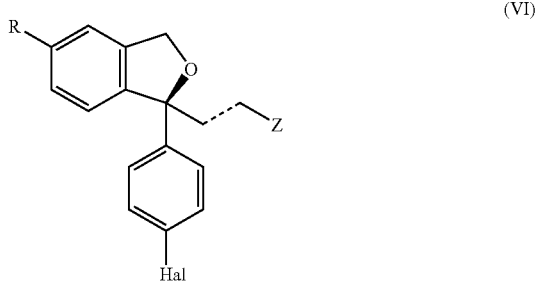

(VI)

wherein R, Z and Hal is as defined above by treatment with a base, optionally followed by, in either order, conversion of the group R to a cyano group, conversion of the group Z to a dimethylaminomethyl group, conversion of Hal to fluoro, and conversion of a dotted line representing a double bond to a single bond; optionally followed by conversion of escitalopram or a derivative of formula (VI) to a salt thereof.

According to another embodiment of the invention, the R group in the compound of formula (IV) the obtained in the form of the S-enantiomer is optionally converted to cyano, the Z group in the compound of formula IV obtained is optionally converted to a dimethylaminomethyl group, Hal is optionally converted to fluoro and/or a dotted line representing a double bond is optionally converted to a single bond, in either order; followed by conversion of the compound of formula (IV) to escitalopram or a derivative thereof

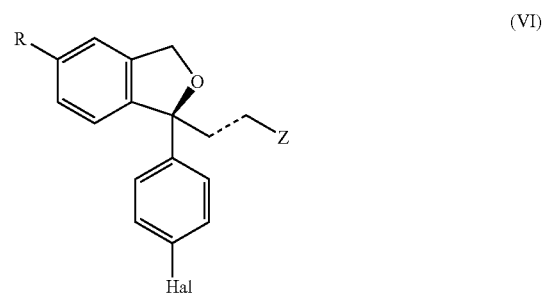

(VI)

wherein R, Z and Hal is as defined above by treatment with a base, optionally followed by, in either order, conversion of the group R to a cyano group, conversion of the group Z to a dimethylaminomethyl group, conversion of Hal to fluoro, and conversion of a dotted line representing a double bond to a single bond; optionally followed by conversion of escitalopram or a derivative of formula (VI) to a salt thereof.

According to the most preferred embodiment of the invention, a mixture of the compound of formula (II) and (IV) wherein R is cyano, the dotted line is a single bond, Z is dimethylaminomethyl, Hal is fluoro, Y is a bond and $R^1$ is —$CH_2$—$CH_2$—$CH_3$ is reacted with a cyclic anhydride of formula (Ia) wherein X is —$(CH_2)_{0-1}$ to form a mixture of the corresponding S-enantiomer of formula (V) and the R-enantiomer of formula (IV). The isolated compound of formula (V) is then treated with NaH to form the compound of formula (VI).

The mixture of formula (II) and (IV) used as starting material is preferably prepared by enzymatic acylation of a compound of formula II wherein R is cyano, the dotted line is a single bond, Z is dimethylaminomethyl, Hal is fluoro, using vinylbutyrate as acylating agent and the enzyme *Candida antartica* lipase B.

DETAILED DESCRIPTION OF THE INVENTION

When used in connection with the compounds of formula (II), (IV), (V) and (VI), the terms "enantiomer", "R-enantiomer", "S-enantiomer", "R-form", "S-form", "R-diol" and "S-diol" refer to the orientation of the groups around the carbon atom to which the 4-Hal-phenyl group is attached.

As used herein, the term $C_{1-10}$-alkyl refers to a branched or unbranched alkyl group having from one to ten carbon atoms inclusive, such as methyl, ethyl, 1-propyl, 2-propyl, 1-butyl, 2-butyl, 2-methyl-2-propyl, 2-methyl-1-propyl, pentyl, hexyl and heptyl. $C_{1-6}$-alkyl refers to a branched or unbranched alkyl group having from one to six carbon atoms inclusive, such as methyl, ethyl, 1-propyl, 2-propyl, 1-butyl, 2-butyl, 2-methyl-2-propyl, 2-methyl-1-propyl, pentyl and hexyl. $C_{1-4}$-alkyl refers to a branched or unbranched alkyl group having from one to four carbon atoms inclusive, such as methyl, ethyl, 1-propyl, 2-propyl, 1-butyl, 2-butyl, 2-methyl-2-propyl and 2-methyl-1-propyl. $C_{1-3}$-alkyl refers to a branched or unbranched alkyl group having from one to three carbon atoms inclusive, such as methyl, ethyl, 1-propyl, 2-propyl.

Similarly, $C_{2-10}$-alkenyl and $C_{2-10}$-alkynyl designate branched or unbranched alkenyl and alkynyl groups respectively, having from two to ten carbon atoms, including one double bond and one triple bond respectively, such as ethenyl, propenyl, butenyl, ethynyl, propynyl and butynyl. $C_{2-6}$-alkenyl and $C_{2-6}$-alkynyl designate branched or unbranched alkenyl and alkynyl groups, respectively, having from two to six carbon atoms, including one double bond and one triple bond respectively, such as ethenyl, propenyl, butenyl, ethynyl, propynyl and butynyl. $C_{2-4}$-alkenyl and $C_{2-4}$-alkynyl designate branched or unbranched alkenyl and alkynyl groups, respectively, having from two to four carbon atoms, including one double bond and one triple bond respectively, such as ethenyl, propenyl, butenyl, ethynyl, propynyl and butynyl. $C_{2-3}$-alkenyl and $C_{2-3}$-alkynyl designate branched or unbranched alkenyl and alkynyl groups, respectively, having from two to three carbon atoms, including one double bond and one triple bond respectively, such as ethenyl, propenyl, ethynyl and propynyl.

The terms $C_{1-10}$-alkoxy, $C_{1-10}$-alkylthio, $C_{1-10}$-alkylamino and di-($C_{1-10}$-alkyl)amino etc. designate such groups in which the alkyl group is $C_{1-10}$-alkyl as defined above. The terms $C_{1-6}$-alkoxy, $C_{1-6}$-alkylthio, $C_{1-6}$-alkylamino and di-($C_{1-6}$-alkyl)amino etc. designate such groups in which the alkyl group is $C_{1-6}$-alkyl as defined above. The terms $C_{1-4}$-alkoxy, $C_{1-4}$-alkylthio, $C_{1-4}$-alkylamino and di-($C_{1-4}$-alkyl) amino etc. designate such groups in which the alkyl group is $C_{1-4}$-alkyl as defined above. The terms $C_{1-3}$-alkoxy, $C_{1-3}$-alkylthio, $C_{1-3}$-alkylamino and di-($C_{1-3}$-alkyl)amino etc. designate such groups in which the alkyl group is $C_{1-3}$ alkyl as defined above.

Halogen means fluoro, chloro, bromo or iodo.

As used herein the term "anti-solvent" designates a liquid which when added to a solvent-solute system reduces the solubility of the solute.

In a particular embodiment of the invention, the separation of the compound of formula (IV) from the ester of formula (V) is performed by allowing the acid of formula (V) to precipitate from the reaction mixture, and separating the precipitate of the compound of formula (V) from the reaction mixture, optionally followed by isolation of the compound of formula (IV) or a salt thereof from the reaction mixture.

In a particular embodiment of the invention, R', R" and R'" are independently selected from hydrogen and $C_{1-6}$-alkyl, and $Q^1$ and $Q^2$ are both carbon.

In a particular embodiment of the invention the mixture of enantiomers of the compound of formula (V) comprises more than 60% of the S-enantiomer of the compound of formula (V), such as more than 70%, more than 80%, more than 90%, more than 95%, more than 98% or more than 99%.

In another equally particular embodiment of the invention the mixture of enantiomers of the compound of formula (V) comprises more than 60% of the R-enantiomer of the compound of formula (V), such as more than 70%, more than 80%, more than 90%, more than 95%, more than 98% or more than 99%.

In yet another equally particular embodiment of the invention the mixture of enantiomers of the acyl derivative of formula (IV) comprises more than 60% of the S-enantiomer of the compound of formula (V), such as more than 70%, more than 80%, more than 90%, more than 95%, more than 98% or more than 99%.

In yet another equally particular embodiment of the invention the mixture of enantiomers of the acyl derivative of formula (IV) comprises more than 60% of the R-enantiomer of the compound of formula (V), such as more than 70%, more than 80%, more than 90%, more than 95%, more than 98% or more than 99%.

In a preferred embodiment of the invention R is halogen or cyano, most preferred cyano.

In a further preferred embodiment of the invention Hal is fluoro.

In a further preferred embodiment of the invention, the dotted line in formula (II), (IV) and (V) is a single bond.

In still a further preferred embodiment Z is dimethylaminomethyl or a group that may be converted to dimethylaminomethyl. In a preferred embodiment Z is dimethylaminomethyl.

Most preferred, Hal is fluoro, R is cyano, the dotted line is a single bond and Z is dimethylaminomethyl.

According to one embodiment of the invention, Y in the compound of formula (IV) is O or S.

According to another embodiment of the invention, Y in the compound of formula (IV) is NH.

However, according to a preferred embodiment of the invention, Y in the compound of formula (IV) is a bond.

Suitably, the substituent $R^1$ in the compound of formula (IV) as defined in any of the embodiments above, is as follows: $R^1$ is $C_{1-6}$-alkyl, $C_{2-6}$-alkenyl or $C_{2-6}$-alkynyl all of which may optionally be substituted one or more times with substituents selected from $C_{1-6}$-alkoxy, $C_{1-6}$-alkylthio, hydroxy, halogen, amino, nitro, cyano, $C_{1-4}$-alkylamino and di-($C_{1-6}$-alkyl)amino, more suitable $R^1$ is $C_{1-4}$-alkyl, $C_{2-4}$-alkenyl or $C_{2-4}$-alkynyl all of which may optionally be substituted one or more times with substituents selected from $C_{1-4}$-alkoxy, $C_{1-4}$-alkylthio, hydroxy, halogen, amino, nitro, cyano, $C_{1-4}$-alkylamino and di-($C_{1-4}$-alkyl)amino, preferably $R^1$ is $C_{1-3}$-alkyl, $C_{2-3}$-alkenyl or $C_{2-3}$-alkynyl all of which may optionally be substituted one or more times with $C_{1-3}$-alkoxy, $C_{1-3}$-alkylthio, hydroxy, halogen, amino, nitro, cyano, $C_{1-3}$-alkylamino and di-($C_{1-3}$-alkyl)amino, more preferred $R^1$ is $C_{1-3}$-alkyl, $C_{2-3}$-alkenyl or $C_{2-3}$-alkynyl, and more suitable $R^1$ is $C_{1-3}$-alkyl, in particular unbranched $C_{1-3}$-alkyl, such as methyl, ethyl or propyl.

The present invention is particularly useful for separation of compounds of formula (II) in the form of the S- or the R-enantiomer and the compound of formula (IV) in the form of the opposite enantiomer obtained by enzymatic resolution according to the processes described in WO application No. PCT/DK/0300537 published as WO2004/014821.

Thus according to an embodiment of the invention, the mixture of a compound of formula (II) and (IV) used in the process is prepared by selective enzymatic acylation or selective enzymatic deacylation.

A particular advantage of the present invention is that following formation, the compound of formula (V) precipitates from the reaction mixture and is thereafter easily isolated.

Another particular advantage of the present invention is that (depending on the particular reagent of formula (Ia)-(Ic) used) it results in the separation and isolation of a product which may be ring closed directly to form escitalopram or a derivative thereof by treatment with a base.

The reaction of the mixture of a compound of formula (II) in the form of one enantiomer with a compound of formula (Ia), (Ib) or (Ic) may be carried out in an inert organic solvent, such as tetrahydrofuran, preferably a solvent in which the acid of formula (V) forms a precipitate and in an amount of the particular solvent where the acid of formula (V) forms a precipitate. Suitable solvents may be identified by the skilled person.

Alternatively the reaction is performed in a solvent from which the acid of formula (V) does not form a precipitate and an anti-solvent is added after formation of the compound of formula (V) whereby the acid of formula (V) forms a precipitate.

The reaction may suitably be carried out at or around room temperature (25° C.).

The compound of formula V is suitably separated from the compound of formula (IV) by filtration or decanting, or by any other suitable way of separating a solid form a liquid.

When the compound of formula V, which is isolated, is an S-enantiomer it may be ring closed directly by treatment with a base in a suitable organic solvent.

Enantioselective ring-closure of an S-enantiomer of formula (V) to form escitalopram or another compound of formula (VI) may suitably be carried out by treatment of the compound of formula (V) with a base such as $KOC(CH_3)_3$ or other alkoxides, NaH or other hydrides, or amines such as triethylamine, ethyldiisopropylamine or pyridine, at low temperatures in an inert organic solvent, such as tetrahydrofuran, toluene, DMSO, DMF, t-butyl methyl ether, dimethoxyethane, dimethoxymethane, dioxane, acetonitrile or dichloromethane. This process may be performed analogously to those described in U.S. Pat. No. 4,943,590.

In the same way, a compound of formula (IV) in the form of the S-enantiomer and separated from the reaction mixture may be subjected to ring closure by treatment with a base.

In some cases, it may be advantageous to exchange the —CW—Y—$R^1$ group in the compound of formula IV or the —CO—V group in the compound of formula (V) for a more labile group, before ring closure is carried out. Such labile groups (leaving groups) could typically be a group selected from methanesulfonyloxy, p-toluene-sulfonyloxy, 10-camphorsulfonyloxy, trifluoroacetyloxy and trifluoromethanesulfonyloxy or halogen.

Typically, the compound of formula (IV) or (V) is then subjected to hydrolysis to form the compound of formula (II) with aqueous base, such as NaOH, KOH or LiOH in water or alcohol or a mixture thereof and then reacted with an activated leaving group, such as a group —O—$SO_2$-A wherein A is $C_{1-6}$-alkyl, $C_{2-6}$-alkenyl, $C_{2-6}$-alkynyl or optionally $C_{1-6}$-alkyl substituted aryl or aryl-$C_{1-6}$ alkyl, particularly mesylchloride or tosylchloride, or trifluoroacetylchloride, acetylchloride or an form of formic acid such as a mixture of formic acid and acetic anhydride in an organic solvent in the presence of an organic base.

Preferably, the substituent V in the compound of formula (V), is a substituent which enable direct ring closure of the compound of formula V by treatment with a base. Most preferred, V is —$CH_2$—$CH_2$—COOH or —$CH_2$—$CH_2$—$CH_2$—COOH.

The optical purity of the escitalopram product may have to be improved after ring closure. Improvement of the optical purity may be obtained by chromatography on a chiral stationary phase or by crystallisation of racemic citalopram base or a salt thereof according to the methods described in WO 03/000672.

The R-enantiomer of the compounds of formula (V) and (IV) obtained according to the invention may be used to prepare racemic citalopram and escitalopram by ring closure in acidic environment according to the method described in WO 03/000672. Suitable acids for carrying out acidic ring closure are mineral acid, a carboxylic acid, a sulfonic acid or sulfonic acid derivative, more suitable $H_2SO_4$ or $H_3PO_4$.

The starting mixture used for the separation method according to the invention may be prepared by enzymatic acylation or deacylation using a hydrolase, such as a lipase, an esterase, an acylase or a protease, as described in WO application No. PCT/DK/0300537 published as WO2004/014821.

It has been found that enzymatic acylation according to the invention may be carried out using Novozyme®435, from *Candida antartica*, LipoZyme™ TL IM from *Thermomyces lanuginosus* both available from the company Novozymes A/S or Lipoprotein Lipase *pseudomonas* sp. (isolated from *Pseudomonas Cepacia* and obtained from Fluka), and particularly good results have been found when using Novozyme 435, from *Candida antartica* or Lipoprotein Lipase *pseudomonas* sp.

The "enzyme" or "hydrolase" may be immobilized as the enzyme itself or as a cell body by known techniques, and may be used in immobilized form. The immobilization may be carried out by methods known to the person skilled in the art, such methods include, for example carrier bonding, cross linking, encapsulation and the like. Thus, the hydrolase may be used in the form of an immobilized enzyme or Cross-Linked Enzyme Crystal (CLEC) enzymes.

The above mentioned enzymes may also be used in the form of cultured products containing the enzyme, such as culture fluid containing a cell body, or a cultured cell body, processed product of the cultured product and any immobilized forms of these enzymes/cultured products.

Mutants, variants or any equivalents of the above specifically mentioned enzymes, which are capable of performing the selective acylation or deacylation may also be used. The variants or equivalents thereof may be isolated from various strains of *Pseudomonas, Candida* or *Thermomyces*, or any other source, or they may be prepared by mutation of the DNA encoding the above-mentioned enzymes leading to variations in the amino acid composition of the enzyme. Suitably the mutants or variants of the above mentioned enzymes are variants and mutants where single amino acids have been removed or replaced by other amino acids, and suitable the amino acid sequence of the variant or mutant is more than 60% identical, preferably more than 80% and most preferred more than 90% identical to the above mentioned enzymes. The preferred reaction conditions for enzymatic acylation/deacylation differ depending on the particular enzyme used, whether it is immobilised or not etc.

A suitable temperature for the reaction lies between 0-80° C., more preferably between 20-60° C., or more preferred between 30-50° C.

The amount of enzyme to be used is not particularly restricted, but is usually 0.01-1.0, preferably 0.02-0.5 and more preferably 0.02-0.3, as weight ratio relative to substrate.

The reaction may be carried out as a batch process or it may be carried out as a continuous process. The enzyme may be used in a plurality of batches repeatedly or continuously. The reaction time is not particularly restricted, and will depend on the enzyme used and the scale and type production method (batch or continuous).

According to WO application No. PCT/DK/0300537 published as WO2004/014821 the acylating agent used for the enzymatic acylation may be a reagent of formula

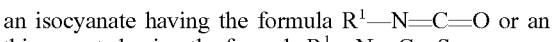
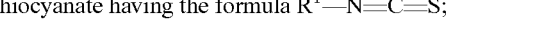

or an isocyanate having the formula $R^1$—N=C=O or an isothiocyanate having the formula $R^1$—N=C=S;

wherein X is O or S; W is O or S; U is O or S, V is halogen;

$R^0$ is $C_{1-10}$-alkyl, $C_{2-10}$-alkenyl or $C_{2-10}$-alkynyl all of which may optionally be substituted one or more times with substituents selected from $C_{1-10}$-alkoxy, $C_{1-10}$-alkylthio, hydroxy, halogen, amino, nitro, cyano, $C_{1-10}$-alkylamino, di-($C_{1-10}$-alkyl)amino, aryl, aryloxy, arylthio and heteroaryl, or $R^0$ is aryl, wherein any of the aryl and heteroaryl groups may optionally be substituted one or more times with substituents selected from $C_{1-10}$-alkyl, $C_{2-10}$-alkenyl, $C_{2-10}$-alkynyl, $C_{1-10}$-alkoxy, $C_{1-10}$-alkylthio, hydroxy, halogen, amino, nitro, cyano, $C_{1-10}$-alkylamino and di-($C_{1-10}$-alkyl)amino;

$R^1$ is as defined for $R^0$;

$R^2$ is as defined for $R^0$, or $R^2$ is a suitable irreversible acyl donor group;

or $R^0$ and $R^1$ together form a chain of 3 to 5 carbon atoms;

provided that W and U is not S when X is S.

Preferably, U is O in the compound of formula (IIIa).
Preferably, W is O in any of the above acylating agents.
Preferably, X is O in any of the above acylating agents.
Preferably, $R^1$ and $R^0$ is $C_{1-3}$-alkyl, in particular unbranched $C_{1-3}$-alkyl, such as methyl, ethyl or propyl and preferably $R^2$ is $C_{1-3}$-alkyl substituted one or more times with halogen or $R^2$ is $C_{2-3}$-alkenyl, and most preferred $R^2$ is $C_{2-3}$-alkenyl, such as vinyl.

A preferred acylating agent is vinyl butyrate.

Enzymatic deacylation may be carried out using a compound of formula

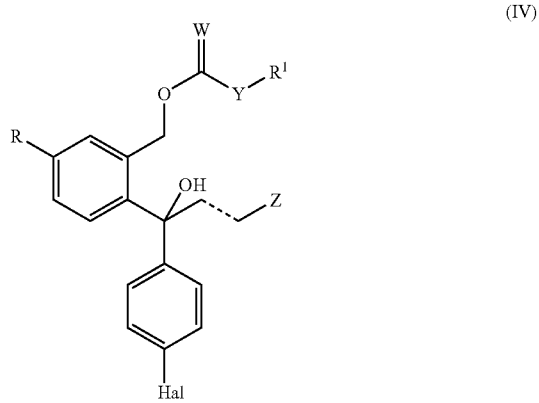

(IV)

wherein R, Z, W, Y, Hal, the dotted line and $R^1$ is as defined above, as starting material.

Suitably, $R^1$ is $C_{1-10}$-alkyl, preferably unbranched $C_{1-10}$-alkyl and more preferred $R^1$ is unbranched $C_{4-10}$-alkyl in the starting material used for enzymatic deacylation.

The selective enzymatic acylation is carried out under conditions substantially suppressing hydrolysis. Hydrolysis, which is the reverse reaction of the acylation reaction, takes place if water is present in the reaction system.

Thus, selective enzymatic acylation is preferably carried out in an anhydrous organic solvent or almost anhydrous organic solvent (enzymes normally require the presence of some water to be active). The percentage of water allowed in a particular reaction system, may be determined by a person skilled in the art.

The organic solvent, which may be used for the acylation reaction, is not particularly important as long as it does not deactivate the enzyme used. Suitable solvents include hydrocarbons such as hexane, heptane, benzene and toluene; ethers such as diethyl ether, diisopropyl ether, tetrahydrofuran, 1,4-dioxane, tert-butyl methyl ether and dimethoxyethane; ketones such as acetone, diethyl ketone, butanon, and methyl ethyl ketone; esters such as methyl acetate, ethyl acetate, ethyl butyrate, vinyl butyrate and ethyl benzoate; halogenated hydrocarbons such as methylene chloride, chloroform and 1,1,1-trichloroethane; secondary and tertiary alcohols, such as tert-butanol; nitrogen-containing solvents such as dimethylformamide, acetoamide, formamide, acetonitrile and propionitrile; and aprotic polar solvents such as dimethylsulfoxide, N-methylpyrrolidone and hexamethylphosphorous triamide.

Among them, hydrocarbons such as hexane, heptane, benzene and toluene, ethers such as diethyl ether, diisopropyl ether, 1,4-dioxane and tert-butyl methyl ether and esters such as vinyl butyrate, are preferred. For one enzyme the most preferred solvents may be ethers and aromatic hydrocarbons such as benzene or toluene, most preferred toluene and for another enzyme the most preferred solvents may be ethers such as 1,4-dioxane. The above solvents may be used singly or in a combination of two or more solvents.

The concentration of racemic diol of formula (II) and acylating agent should not be too high as a high concentration of reagents in the solvent may lead to non-selective acylation of the racemic diol of formula (II). Suitable the concentration of racemic diol of formula (II) and acylating reagent is each below 1.0 M, more suitable below 0.5 M, even more suitable below 0.2 M or even more suitable below 0.1 M. A person skilled in the art will be able to determine the optimal concentration of racemic diol of formula (II) and acylating agent.

Selective enzymatic deacylation is preferably carried out in water or a mixture of water and an organic solvent, suitable in presence of a buffer. The organic solvent, which may be used in the reaction, is not particularly important as long as it does not deactivate the enzyme used. Suitable organic solvents are solvents miscible with water such as alcohols, acetonitrile, DMF, DMSO, dioxane, DME and diglyme. The skilled person will be able to identify other suitable solvents. A person skilled in the art will be able to determine the optimal concentration of racemic compound of formula (IV) used in the reaction The stereoselectivity of the enzyme used, may be increased by carrying out the acylation or deacylation in presence of an organic acid and/or an organic base.

In particular the enzymatic acylation or enzymatic deacylation is carried out in the presence of an organic acid, suitable an organic carboxylic acid.

Suitably the above-mentioned organic acid is an aromatic carboxylic acid or an aliphatic carboxylic acid.

Suitable organic acids, which may be used in the reaction, are, alkylcarboxylic acids, cycloalkylcarboxylic acids, cycloalkylalkylcarboxylic acids, optionally substituted phenylalkylcarboxylic acids and optionally substituted phenylcarboxylic acids. Suitable aliphatic carboxylic acids, are carboxylic acids such as formic acid, acetic acid, propionic acid, n-butyric acid, iso-butyric acid, 2-ethylbutyric acid, n-valeric acid, iso-valeric acid, pivalic acid, n-caproic acid, iso-caproic acid, decanoic acid, crotonic acid, palmitic acid, cyclopentanecarboxylic acid, cyclohexanecarboxylic acid, phenyl-$C_{1-4}$-alkylcarboxylic acids such as 3-phenylpropionic acid, 4-phenylbutyric acid, oxalic acid, malonic acid and tartaric acid. Suitable aromatic carboxylic acids, includes acids such as benzoic acid, p-chlorobenzoic acid, p-nitrobenzoic acid, p-methoxybenzoic acid, p-toluic acid, o-toluic acid, m-toluic acid, naphthoic acid, phthalic acid and terephthalic acid, salicylic acid, hydrocinnamic acid for instance.

Preferably, the organic acid used to improve stereoselectivity of the enzyme is selected from n-propionic acid, iso-propionic acid, n-butyric acid, iso-butyric acid, iso-valeric acid, 2-ethylbutyric acid, crotonic acid, palmitic acid, cyclohexane-carboxylic acid, pivalic acid, benzoic acid and p-toluic acid, salicylic acid and 3-phenylpropionic acid. Most preferred, the carboxylic acid used is pivalic acid.

The amount of the organic acid to be used is not particularly restricted, but the molar ratio relative to a substrate is usually 0.1 to 10, preferably 1.0 to 3.0, and more preferably 1.0 to 2.0.

Alternatively, an organic base may be used to improve selectivity of the enzyme, either alone or together with any of the above-mentioned organic acid. As suitable organic base there may be mentioned, triethylamine, pyridine and 4-dimethylamino-pyridine, and pyridine is preferred. Suitable combinations of organic acid and organic base are benzoic acid and pyridine for example.

The amount of the organic base to be used is not particularly restricted, but the molar ratio relative to a substrate is usually 0.5 to 3.0, and preferably 0.5 to 2.0.

As mentioned above, the group R means cyano or any other group that may be converted to a cyano group.

Groups that may be converted to a cyano group include halogen such as chloro, bromo, iodo or fluoro, preferably chloro or bromo.

Other groups which may be converted to cyano include $CF_3$—$(CF_2)_n$—$SO_2$—O—, wherein n is 0-8, —OH, —CHO, —$CH_2OH$, —$CH_2NH_2$, —$CH_2NO_2$, —$CH_2Cl$, —$CH_2Br$, —$CH_3$, —$NHR^5$, —CHNOH, —$COOR^6$, —$CONR^6R^7$ wherein $R^5$ is hydrogen or $C_{1-6}$-alkylcarbonyl, and $R^6$ and $R^7$ are selected from hydrogen, optionally substituted $C_{1-6}$-alkyl, aryl-$C_{1-6}$-alkyl or aryl and, a group of formula

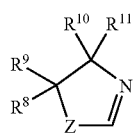

(VII)

wherein Z is O or S; $R^8$-$R^9$ are each independently selected from hydrogen and $C_{1-6}$-alkyl or $R^8$ and $R^9$ together form a $C_{2-5}$-alkylene chain thereby forming a spiro ring; $R^{10}$ is selected from hydrogen and $C_{1-6}$-alkyl, $R^{11}$ is selected from hydrogen, $C_{1-6}$-alkyl, a carboxy group or a precursor group therefore, or $R^{10}$ and $R^{11}$ together form a $C_{2-5}$-alkylene chain thereby forming a spiro ring.

When R is halogen, in particular bromo or chloro, conversion to a cyano may be carried out as described in U.S. Pat. No. 4,136,193, WO 00/13648, WO 00/11926 and WO 01/02383.

According to U.S. Pat. No. 4,136,193 conversion of a bromo group to a cyano group, is carried out by reaction with CuCN.

WO 00/13648 and WO 00/11926 describe the conversion of a halogen or a triflate group to a cyano group by cyanation with a cyanide source in presence of a Pd or Ni catalyst.

Compounds wherein the group R is a group of formula (VII) may be converted to the corresponding cyano compound by methods analogous to those described in WO 00/23431.

Compounds wherein R is OH, —$CH_2OH$, —$CH_2NH_2$, —$CH_2NO_2$, —$CH_2Cl$, —$CH_2Br$, —$CH_3$ or any of the groups above, may be converted to the corresponding cyano compounds by methods analogous to those described in WO 01/68632.

Racemic compounds of formula (II) may be prepared by the methods described in the above-mentioned patents or by the allylation method described in U.S. Pat. No. 4,136,193 or the double grignard reaction described in EP 171 943 or by analogous methods. Racemic compounds of formula (IV) may be prepared from racemic compounds of formula (II) by non-selective acylation using anhydrides, esters, carbonates, isocyanates or isothiocyanates as defined by formulas (IIIa), (IIIb), (IIIc), $R^1$—N=C=O and $R^1$—N=C=S above.

In some cases the racemic compound of formula (II) may be available in the form of an acid addition salt, such as the sulphate salt, and in this case a free base of the compound of formula (II) may be obtained by treating the salt with a base in a mixture or water and an organic solvent, to transfer the compound of formula (II) into the organic phase.

Preferably, R is cyano. If R is not cyano, conversion of the group R to a cyano group is suitably carried out after ring closure to form a compound of formula (VI).

Preferably, Hal if fluoro. If Hal is not fluoro, conversion of the group Hal to a fluoro is suitably carried out after ring closure to form a compound of formula (VI). A procedure for carrying out this conversion is described in Speciality Chemicals Magazine, April 2003, page 36-38.

Z groups which may be converted to dimethylaminomethyl are groups such as —$CH_2$-L, —$CH_2$—$NO_2$, —MgHal, cyano, aldehyde, —$CH_2$—O—Pg, —$CH_2$—$NPg_1Pg_2$, —$CH_2$—$NMePg_1$, —$CH_2NHCH_3$, —$CH_2$—$NH_2$, —CO—$N(CH_3)_2$, —$CH(A^1R^{12})(A^1R^{13})$, -$(A^1R^{14})(A^2R^{15})(A^3R^{16})$, —$COOR^{17}$, —$CH_2$—CO—$NH_2$, —CH=CH—$R^{18}$ or —$CONHR^{19}$, wherein Pg is a protection group for an alcohol group, $Pg_1$ and $Pg_2$ are protection groups for an amino group, $R^{12}$ and $R^{13}$ are independently selected from $C_{1-6}$-alkyl, $C_{2-6}$-alkenyl, $C_{2-6}$-alkynyl and optionally alkyl substituted aryl or aralkyl groups or $R^{12}$ and $R^{13}$ together form a chain of 2 to 4 carbon atoms, each of $R^{14}$-$R^{18}$ are independently selected from $C_{1-6}$-alkyl, $C_{2-6}$-alkenyl, $C_{1-6}$-alkynyl and optionally $C_{1-6}$-alkyl substituted aryl or aryl-$C_{1-6}$-alkyl, $R^{19}$ is hydrogen or methyl and $A^1$, $A^2$ and $A^3$ are selected form O and S; L is a leaving group, such as halogen or —O—$SO_2$-A wherein A is $C_{1-6}$ alkyl, $C_{2-6}$ alkenyl, $C_{2-6}$ alkynyl or optionally $C_{1-6}$-alkyl substituted aryl or aryl-$C_{1-6}$-alkyl.

The alcohol-protecting group, Pg, may be a trialkylsilyl group, a benzyl group or a tetrahydropyranyl group (THP).

Suitable groups $Pg_1$ and $Pg_2$ are aralkyl or —$SO_2$—$R^0$ groups wherein $R^0$ is alkyl, aralkyl, aryl or aryl substituted with alkyl, typically methyl, benzyl or tosyl, or $Pg_1$ and $Pg_2$ together with the N atom to which they are attached form an optionally substituted phthalimide group.

Compounds wherein Z is —$CH_2$—O—Pg may be converted to the corresponding compounds wherein Z is dimethylaminomethyl as described in WO 01/43525, WO 01/51478 or WO 01/68631 or by analogous methods.

Compounds wherein Z is —$CH_2$-L, wherein L is a leaving group, may be converted to a dimethylaminomethyl group in the same manner.

Compounds wherein Z is —CO—$N(CH_3)_2$ and —CO—$NHR^{19}$, wherein $R^{19}$ is hydrogen or methyl, may be converted to the corresponding compounds wherein Z is dimethylaminomethyl as described in WO 01/43525 or WO 01/68631 or by analogous methods.

Compounds wherein Z is —$CH_2$—NMe($Pg_1$) or —$CH_2$—N(Pg1)(Pg2) may be converted to the corresponding compound wherein Z is dimethylaminomethyl as described in WO 01/43525 or WO 01/68631 or by analogous methods.

Compounds wherein Z is —CH(A$^1$R$^{12}$)(A$^2$R$^{13}$) may be converted to the corresponding compounds wherein Z is dimethylaminomethyl as described in WO 01/43525 or WO 01/68631 or by analogous methods.

Compounds wherein Z is —C(A$^1$R$^{14}$)(A$^2$R$^{15}$)(A$^3$R$^{16}$) may be converted to the corresponding compounds wherein Z is dimethylaminomethyl as described in WO 01/68631 or by analogous methods.

Compounds wherein Z is —COOR$^{17}$ may be converted to the corresponding compounds wherein Z is dimethylaminomethyl as described above, starting with the carboxylic acid ester.

Compounds wherein Z is —CH$_2$—CONH$_2$ may be converted to the corresponding compound wherein Z is as described in WO 01/43525 or WO 01/68631 or by analogous methods.

Compounds wherein Z is —CH=CHR$^{18}$ may be converted to the corresponding compound wherein Z is dimethylaminomethyl as described in WO 01/43525 or WO 01/68631 or by analogous methods.

Compounds wherein Z is cyano or —CH$_2$—NO$_2$ may be converted to the corresponding compound wherein Z is dimethylaminomethyl as described in WO 01/68629 or by analogous methods.

Compounds wherein Z is —MgHal may be converted to the corresponding compound wherein Z is dimethylaminomethyl as described in WO 01/68629 or by analogous methods.

Preferably, Z is dimethylaminomethyl. If Z is not dimethylaminomethyl, conversion of Z to a dimethylaminomethyl group is suitably carried out after ring closure.

Compounds wherein the dotted line represents a double bond may be converted to the corresponding compound wherein the dotted line is a single bond by the methods described in WO 01/68630 or by analogous methods. Preferably the reduction is carried out after ring closure.

EXPERIMENTAL

In the following examples % conversion and optical purity were measured and calculated as described below:

HPLC analysis condition (for conversion rate):

Column: A Lichrospher RP-8 column, 250×4 mm (5 μm particle size)

Eluent: Buffered MeOH/water prepared as follows: 1.1 ml Et$_3$N added to 150 ml water, 10% H$_3$PO$_4$(aq) is added to pH=7 and water is added to a total of 200 ml. The mixture is added to 1.8 L MeOH.

Temperature: 35° C.
Flow rate: 1 mL/min
Pressure: 16.0 MPa
Detection: UV 254 nm
Injection volume: 10 microL Conversion rate(%)=$P/(S+P)\times100$, ($P$: amount of product, $S$: amount of residual substrate).

Super critical fluid chromatography. Analysis condition (for optical purity):

Column: Daicel AD column with the dimensions 250×4.6 mm (5 μm particle size)

Mobile phase: Carbon dioxide

Modifier: Methanol with diethylamine (0.5%) and trifluoroacetic acid (0.5%).

Modifier gradient:
1-2% in 4 minutes
2-4% in 4 minutes
4-8% in 4 minutes
8-16% in 4 minutes
16-32% in 4 minutes
32-45% in 1.62 minutes
Temperature: Ambient temperature
Flow rate: 2 mL/min
Pressure: 20 mPa
Detection: UV 230 nm and 254 nm
Injection volume: 10 microL Optical purity(% $ee$)=$(A-B)/(A+B)\times100$, ($A$ and $B$ represent corresponding stereo isomer, $A>B$)

$E$-value=$\ln((1-c/100)\times(1-Es/100))/\ln((1-c/100)\times(1+Es/100))$ ($c$: conversion ratio, $Es$: optical purity of residual substrate)

EXAMPLE 1

(S)-1-(3-dimethylamino-propyl)-1-(4-fluoro-phenyl)-1,3-dihydro-isobenzofuran-5-carbonitrile Hydrogen Oxalate To a mixture of 3.7 g 4-[(S)-4-dimethylamino-1-(4'-fluorophenyl)-1-hydroxybutyl]-3-hydroxymethylbenzonitrile and 6.3 g butyric acid 5-cyano-2-[4-dimethylamino-1-(4-fluorophenyl)-1-hydroxybutyl]-benzyl ester (R/S=3:1) in 50 ml tetrahydrofuran was added 1.2 g (1.1 eq.) succinic anhydrid. Allowed to stir overnight at room temperature. Precipitated succinic acid mono-{5-cyano-2-[(S)-4-dimethylamino-1-(4-fluorophenyl)-1-hydroxybutyl]-benzyl} ester was filtered off and washed with cold tetrahydrofuran to obtain 3.1 g ester 98% pure. Crystals were dried in oven and subsequently dissolved in 50 ml anhydrous dimethylformamide. To the solution was added 1.1 g NaH (60% suspension in oil) and stirred overnight at room temperature. The mixture was quenched with water and extracted with 3 times 50 ml diethylether. The combined organic phases were washed with 50 ml water and dried with Na$_2$SO$_4$ and evaporated in vacuo. The remaining oil was dissolved in 14 ml acetone and 630 mg oxalic acid was added. After 1 h stirring at room temperature, the precipitated crystals were filtered off and washed with cold acetone to obtain 2.02 g escitalopram hydrogen oxalate (ee-value 95%)

EXAMPLE 2

Preparation of the Mixture Used in Example 1

(S)-4-[4-Dimethylamino-1-(4'-fluorophenyl)-1-hydroxybutyl]-3-hydroxymethyl-benzonitrile To a stirred solution of racemic 4-[4-Dimethylamino-1-(4-fluorophenyl)-1-hydroxybutyl]-3-hydroxymethylbenzonitrile (29 mmol, 10 g) and vinylbutyrate (58 mmol, 7.5 ml) in anhydrous 1,4-dioxane (142.5 ml) is added lipoprotein lipase *pseudomonas* sp. (160 U, 250 mg). The reaction is heated to 50° C. and followed by HPLC. After 192 hours at a conversion of 41%, additional 250 mg lipase was added. After 504 hours, at a conversion of 63% the reaction was stopped. The enzyme is filtered off and washed with a small amount of 1,4-dioxane. The combined organic phases are evaporated in vacuo and subsequently analyzed on super critical fluid chromatography. Obtained ee-value ((S-diol)=95% (S-diol/R-diol=40:1).

The invention claimed is:
1. A method for the isolation and purification of a compound having the formula

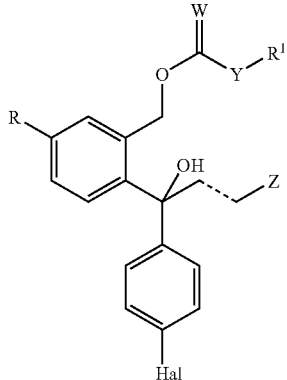

(IV)

wherein R is cyano, halogen, $CF_3$—$(CF_2)_n$—$SO_2$—O—, —CHO, —$CH_2NO_2$, —$CH_2Cl$, —$CH_2Br$, —$CH_3$, —$COOR^6$, —$CONR^6R^7$, or a group of formula

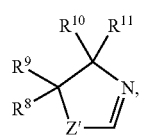

(VII)

wherein
n is 0-8,
$R^6$ and $R^7$ are independently selected from optionally substituted $C_{1-6}$-alkyl, optionally substituted aryl-$C_{1-6}$-alkyl, and optionally substituted aryl,
Z' in formula (VII) is O or S,
$R^8$ and $R^9$ are independently hydrogen or $C_{1-6}$-alkyl or $R^8$ and $R^9$ together form a $C_{2-5}$-alkylene chain thereby forming a spiro ring,
$R^{10}$ is hydrogen or $C_{1-6}$-alkyl, and
$R^{11}$ is hydrogen, $C_{1-6}$-alkyl, a carboxy group, or a precursor group thereto, or $R^{10}$ and $R^{11}$ together form a $C_{2-5}$-alkylene chain thereby forming a spiro ring,
the dotted line represents a double or single bond,
Hal is halogen,
Z is a dimethylaminomethyl group, —$CH_2$-L, —$CH_2$—$NO_2$, cyano, aldehyde, —$CH_2$—O-Pg, —$CH_2$—$NPg_1Pg_2$, —$CH_2$—$NMePg_1$, —CO—$N(CH_3)_2$, —CH$(A^1R^{12})(A^1R^{13})$, -$(A^1R^{14})(A^2R^{15})(A^3R^{16})$, —$COOR^{17}$, or —CH=CH—$R^{18}$, wherein
Pg is a protection group for an alcohol group,
$Pg_1$ and $Pg_2$ are each independently a protection group for an amino group,
$R^{12}$ and $R^{13}$ are independently $C_{1-6}$-alkyl, $C_{2-6}$-alkenyl, $C_{2-6}$-alkynyl, or an optionally alkyl-substituted aryl or aralkyl group, or $R^{12}$ and $R^{13}$ together form a chain of 2 to 4 carbon atoms,
each of $R^{14}$-$R^{18}$ are independently $C_{1-6}$-alkyl, $C_{2-6}$-alkenyl, $C_{2-6}$-alkynyl, or optionally $C_{1-6}$-alkyl-substituted aryl or aryl-$C_{1-6}$-alkyl,
$A^1$, $A^2$ and $A^3$ are independently O or S, and
L is a leaving group, W is O or S,
Y is a bond, O, S or NH,
and $R^1$ is $C_{1-10}$-alkyl, $C_{2-10}$-alkenyl or $C_{2-10}$-alkynyl all of which may optionally be substituted with one or more substituents selected from $C_{1-10}$-alkoxy, $C_{1-10}$-alkylthio, halogen, nitro, cyano, di-($C_{1-10}$-alkyl)amino, aryl, aryloxy, arylthio and heteroaryl, or $R^1$ is aryl, wherein any of the aryl and heteroaryl groups may optionally be substituted one or more times with substituents selected from $C_{1-10}$-alkyl, $C_{2-10}$-alkenyl, $C_{2-10}$-alkynyl, $C_{1-10}$-alkoxy, $C_{1-10}$-alkylthio, halogen, nitro, cyano, and di-($C_{1-10}$-alkyl)amino, or a salt thereof,
and/or a diol of formula

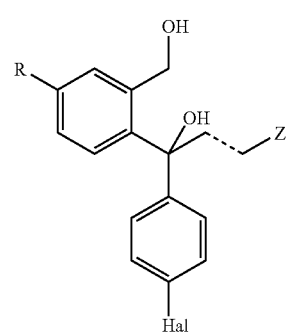

(II)

wherein R, Z, Hal and the dotted line are as defined above, or a salt thereof, from a mixture containing the compound of formula (IV) and the diol of formula (II), comprising:
a) reacting said mixture containing the compound of formula (IV) and the diol of formula (II) with a cyclic anhydride or imide of formula

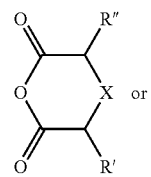

(Ia)

or

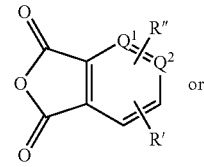

(Ib)

or

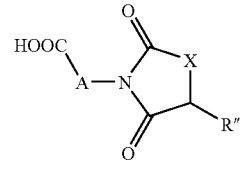

(Ic)

wherein X is —$(CHR''')_n$—, wherein n is 0-2;
and R', R", and R''' are independently selected from hydrogen, $C_{1-6}$-alkyl, $C_{1-6}$-alkoxy, aryloxy, $C_{1-6}$-acyloxy, and aryl-CO—O, wherein each aryl may be substituted with $C_{1-6}$-alkyl, or R' and R" in an anhydride of formula (Ia) together are —O—$CR^4R^5$—

O—, wherein $R^4$ and $R^5$ are independently hydrogen or $C_{1-6}$-alkyl, or R' and R" in an anhydride of formula (Ib) are adjacent and together with the two carbon atoms to which they are attached form a benzene ring;
one of $Q^1$ and $Q^2$ is nitrogen and the other is carbon, or both are carbon;
A is $C_{1-6}$-alkylene, phenylene, or naphthylene wherein the $C_{1-6}$-alkylene, phenylene, or naphthylene groups may optionally be substituted one or more times with $C_{1-6}$-alkyl;

to form a mixture of the compound of formula (IV) and an ester having the formula

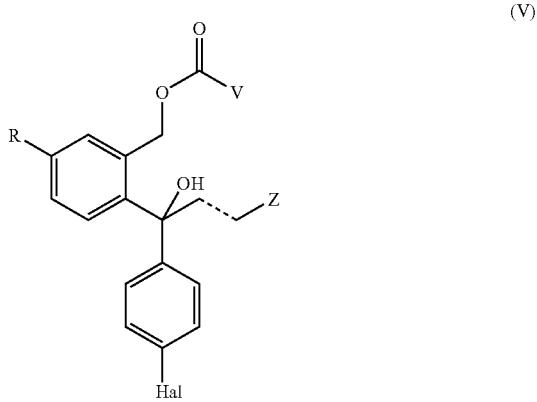

(V)

wherein R, Z and Hal are as defined above and V is —CHR'—X—CR"—COOH, —X—CHR"—CO—NH-A-COOH, —CHR"—X—CO—NH-A-COOH,

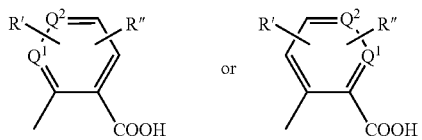

wherein R', R", X, and A are as defined above;
b) separating the compound of formula (IV) from the ester of formula (V) by a method selected from the group consisting of:
 i) allowing the acid of formula (V) or a salt thereof to precipitate from the reaction mixture, and separating the precipitate of the compound of formula (V) or a salt thereof from the reaction mixture, optionally followed by isolation of the compound of formula (IV) or a salt thereof from the reaction mixture;
 ii) partitioning between an organic solvent and an aqueous solvent whereby the compound of formula (IV) will be dissolved in the organic phase whereas the compound of formula (V) will be dissolved in the aqueous phase, separating the phases, and optionally isolating the compound of formula (IV) or a salt thereof and/or isolating the compound of formula (V) or a salt thereof; and
 iii) adsorbing the compound of formula (V) on a basic resin, separating the solvent containing the compound of formula (IV) from the resin, desorbing the compound of formula (V) from the basic resin, and optionally isolating the compound of formula (IV) or a salt thereof and/or isolating the compound of formula (V) or a salt thereof.

2. The method according to claim 1, wherein the separation of the compound of formula (IV) from the ester of formula (V) is performed by allowing the acid of formula (V) or a salt thereof to precipitate from the reaction mixture, and separating the precipitate of the compound of formula (V) of a salt thereof from the reaction mixture, optionally followed by isolation of the compound of formula (IV) or a salt thereof from the reaction mixture.

3. The method according to claim 1, wherein R', R", and R'" are independently selected from hydrogen and $C_{1-6}$-alkyl, and $Q^1$ and $Q^2$ are both carbon.

4. The method according to claim 1, wherein the S-enantiomer of the compound of formula (V) or a mixture of enantiomers of the compound of formula (V) comprising more than 50% of the S-enantiomer of the compound of formula (V) is separated from the R-enantiomer of the acyl derivative of formula (IV) or from a mixture of enantiomers of the acyl derivative of formula (IV) comprising more than 50% of the R-enantiomer of the acyl derivative of formula (IV).

5. The method according to claim 4 wherein the S-enantiomer of the compound of formula (V) is separated from the R-enantiomer of the acyl derivative of formula (IV) or from a mixture of enantiomers of the acyl derivative of formula (IV) comprising more than 50% of the R-enantiomer of the acyl derivative of formula (IV).

6. The method according to claim 5 wherein the S-enantiomer of the compound of formula (V) is separated from the R-enantiomer of the acyl derivative of formula (IV).

7. The method according to claim 1, wherein the S-enantiomer of the acyl derivative of formula (IV) or a mixture of enantiomers of the acyl derivative of formula (IV) comprising more than 50% of the S-enantiomer of the acyl derivative of formula (IV) is separated from the R-enantiomer of the compound of formula (V) or from a mixture of enantiomers of the compound of formula (V) comprising more than 50% of the R-enantiomer of the compound of formula (V).

8. The method according to claim 7 wherein the S-enantiomer of the acyl derivative of formula (IV) is separated from the R-enantiomer of the compound of formula (V) or from a mixture of enantiomers of the compound of formula (V) comprising more than 50% of the R-enantiomer of the compound of formula (V).

9. The method according to claim 8 wherein the S-enantiomer of the acyl derivative of formula (IV) is separated from the R-enantiomer of the compound of formula (V).

10. The method according to claim 4, wherein the compound of formula (V) is obtained in the form of the S-enantiomer, and wherein R is optionally converted to cyano, Z is optionally converted to a dimethylaminomethyl group, Hal is optionally converted to fluoro, and/or a dotted line representing a double bond is optionally converted to a single bond, in any order, followed by conversion of the compound of formula (V) to escitalopram or a derivative thereof having the formula

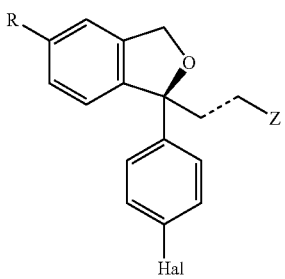

(VI)

wherein R, Z and Hal are as defined above provided that Z is not cyano, by treatment with a base, optionally followed by, in any order, conversion of R to a cyano group, conversion of Z to a dimethylaminomethyl group, conversion of Hal to fluoro, and conversion of a dotted line representing a double bond to a single bond; optionally followed by conversion of escitalopram or a derivative of formula (VI) to a salt thereof.

11. The method according to claim 7, wherein the compound of formula (IV) is obtained in the form of the S-enantiomer, and wherein R is optionally converted to cyano, Z is optionally converted to a dimethylaminomethyl group, Hal is optionally converted to fluoro and/or a dotted line representing a double bond is optionally converted to a single bond, in any order, followed by conversion of the compound of formula (IV) to escitalopram or a derivative thereof having the formula

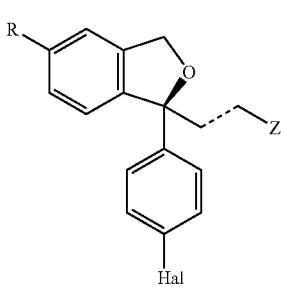

(VI)

wherein R, Z and Hal are as defined above provided that Z is not cyano, by treatment with a base, optionally followed by, in any order, conversion of R to cyano, conversion of Z to a dimethylaminomethyl group, conversion of Hal to fluoro, and conversion of a dotted line representing a double bond to a single bond; optionally followed by conversion of escitalopram or a derivative of formula (VI) to a salt thereof.

12. The method according to claim 10, wherein the basic ring closure is carried out by treatment with a base.

13. The method according to claim 1, wherein Hal is fluoro and R is halogen or cyano.

14. The method according to claim 1, wherein the dotted line represents a single bond.

15. The method according to claim 1, wherein Z is a dimethylaminomethyl group or a group that may be converted to a dimethylaminomethyl group.

16. The method according to claim 1, wherein the cyclic anhydride is a compound of formula (Ia).

17. The method according to claim 16, wherein the cyclic anhydride is succinic anhydride or glutaric anhydride.

18. The method according to claim 1, wherein the cyclic anhydride is a compound of formula (Ib).

19. The method according to claim 18, wherein the cyclic anhydride is phthalic acid anhydride.

20. The method according to claim 1, wherein the imide is a compound of formula (Ic).

21. The method according to claim 20 wherein the imide is N-phenyl-succinimide substituted in the phenyl ring with a carboxy group.

22. The method according to claim 1, wherein Y in the compound of formula (IV) is a bond.

23. The method according to claim 1, wherein Y in the compound of formula (IV) is O or S.

24. The method according to claim 23 wherein Y in the compound of formula (IV) is O.

25. The method according to claim 1, wherein Y in the compound of formula (IV) is NH.

26. The method according to claim 1, wherein $R^1$ is selected from $C_{1-4}$-alkyl, $C_{2-4}$-alkenyl and $C_{2-4}$-alkynyl all of which may optionally be substituted one or more times with substituents selected from $C_{1-4}$-alkoxy, $C_{1-4}$-alkylthio, halogen, nitro, cyano, $C_{1-4}$-alkylamino and di-($C_{1-4}$-alkyl)amino.

27. The method according to claim 26 wherein $R^1$ is selected from $C_{1-3}$-alkyl, $C_{2-3}$-alkenyl and $C_{2-3}$-alkynyl all of which may optionally be substituted one or more times with substituents selected from $C_{1-3}$-alkoxy, $C_{1-3}$-alkylthio, halogen, nitro, cyano, $C_{1-3}$-alkylamino and di-($C_{1-3}$-alkyl)amino.

28. The method according to claim 26 wherein $R^1$ is $C_{1-4}$-alkyl.

29. The method according to claim 27 wherein $R^1$ is $C_{1-3}$-alkyl.

30. The method of claim 29, wherein $R^1$ is methyl, ethyl, or propyl.

31. The method according to claim 1, wherein the mixture of the compound of formula (IV) and the diol of formula (II) is prepared by selective enzymatic acylation or selective enzymatic deacylation.

32. A method for the manufacture of escitalopram, comprising the method of claim 1.

33. The method according to claim 12, wherein the base is selected from alkoxides, hydrides, or amines.

34. The method according to claim 33, wherein the base is selected from $KOC(CH_3)_3$, NaH, triethylamine, ethyldiisopropylamine, and pyridine.

35. The method according to claim 11, wherein the basic ring closure is carried out by treatment with a base.

36. The method according to claim 35, wherein the base is selected from alkoxides, hydrides, or amines.

37. The method according to claim 36, wherein the base is selected from $KOC(CH_3)_3$, NaH, triethylamine, ethyldiisopropylamine, and pyridine.

38. The method according to claim 13, wherein R is cyano.

39. The method according to claim 15, wherein Z is a dimethylaminomethyl group.

40. The method according to claim 30, wherein $R^1$ is propyl.

41. The method according to claim 1, wherein Pg is a trialkylsilyl group, benzyl group, or tetrahydropyranyl group (THP).

42. The method according to claim 1, wherein $Pg_1$ and $Pg_2$ are independently aralkyl or $-SO_2-R^0$, where $R^0$ is alkyl, aralkyl, aryl or aryl substituted with alkyl, or $Pg_1$ and $Pg_2$ together with the N atom to which they are attached form an optionally substituted phthalimide group.

* * * * *